(12) United States Patent
Lee et al.

(10) Patent No.: US 9,816,118 B2
(45) Date of Patent: Nov. 14, 2017

(54) CONTINUOUS PRODUCTION METHOD FOR 5-AMINOLEVULINIC ACID BY USING PHOTOSYNTHETIC MEMBRANE VESICLE

(71) Applicant: SOGANG UNIVERSITY RESEARCH FOUNDATION, Seoul (KR)

(72) Inventors: Jeong Kug Lee, Seoul (KR); Hyeon Jun Kim, Seoul (KR); Eui Jin Kim, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 0 days.

(21) Appl. No.: 14/932,237

(22) Filed: Nov. 4, 2015

(65) Prior Publication Data

US 2016/0122788 A1 May 5, 2016

(30) Foreign Application Priority Data

Nov. 4, 2014 (KR) .................. 10-2014-0151907

(51) Int. Cl.
| | |
|---|---|
| C12P 13/00 | (2006.01) |
| C12P 13/04 | (2006.01) |
| C12N 9/00 | (2006.01) |
| C12N 9/10 | (2006.01) |
| C12N 1/20 | (2006.01) |

(52) U.S. Cl.
CPC .............. *C12P 13/001* (2013.01); *C12N 1/20* (2013.01); *C12N 9/1029* (2013.01); *C12N 9/93* (2013.01); *C12Y 203/01037* (2013.01); *C12Y 602/01004* (2013.01)

(58) Field of Classification Search
None
See application file for complete search history.

(56) References Cited

FOREIGN PATENT DOCUMENTS

| | | |
|---|---|---|
| KR | 10-2001-0102752 A | 11/2001 |
| KR | 10-2013-0075319 A | 7/2013 |

OTHER PUBLICATIONS

Bo Wang et al., Application of synthetic biology in cyanobacteria and algae, Frontiers in Microbiology, vol. 3, Article 344 pp. 1-15, Sep. 2012.

J. D. Tucker et al., Membrane invagination in Rhodobacter sphaeroides is initiated at curved regions of the cytoplasmic membrane, then forms both budded and fully detached spherical vesicles, Molecular Microbiology, (2010), 76, pp. 833-847.

C. A. Rebeiz et al., Photodynamic herbicides: 1. Concept and phenomenology, Enzyme Microb. Technol., 1984, vol. 6, September, pp. 390-401.

Malgorzata Wachowska et al., Aminolevulinic Acid (ALA) as a Prodrug in Photodynamic Therapy of Cancer, Molecules 2011, 16, pp. 4140-4164.

Zhen Kang et al., Metabolic engineering to improve 5-aminolevulinic acid production, Bioengineered Bugs, 2:6, pp. 1-4; Nov./Dec. 2011.

Samuel I. Beal et al., Chemical Synthesis of 4,5-Dioxovaleric Acid and Its Nonenzymatic Transamination to 5-Aminolevulinic Acid, Phytochemistry, 1979, vol. 18, pp. 441-444.

Germaine Cohen-Bazire et al., Kinetic Studies of Pigment Synthesis by Non-Sulfur Purple Bacteria, Journal of Cellular and Comparative Physiology, vol. 49, Issue 1, pp. 25-68, Feb. 1957.

W. R. Sistrom, The Kinetics of the Synthesis of Photopigments in R hodopseudomonas spheroides, J . gen MicroMol. (1962), 28, pp. 607-616.

Marie E. Fraser et al., A Detailed Structural Description of *Escherichia coli* Succinyl-CoA Synthetase, J. Mol. Biol. (1999) 285, pp. 1633-1653.

Eui-Jin Kim et al., Competitive Inhibitions of the Chlorophyll Synthase of *Synechocystis* sp. Strain PCC 6803 by Bacteriochlorophyllide a and the Bacteriochlorophyll Synthase of Rhodobacter sphaeroides by Chlorophyllide a, Journal of Bacteriology, vol. 192, No. 1, Jan. 2010, pp. 198-207.

W. A. Bridge et al., Succinyl Coenzyme A Synthetase from *Escherichia coli*, J. Biol. Chem. 159, 21 (1945), pp. 70-75, Bridger et al.

Bruce F. Burnham, Delta-Aminolevulinic Acid Synthase (Rhodopseudomonas spheroides), Methods in Enzymology 17, pp. 195-200 (1970).

*Primary Examiner* — Michelle F Paguio Frising
(74) *Attorney, Agent, or Firm* — The PL Law Group, PLLC (57) ABSTRACT

A method of continuously producing 5-aminolevulinic acid employs the photosynthetic bacteria-derived photosynthetic membrane vesicle, succinyl-CoA synthetase, and 5-aminolevulinic acid synthase. The enzymatic synthesis of 5-aminolevulinic acid directly from succinic acid and glycine may be simple, but the synthesis is not inexpensive due to the supply of ATP and CoA, which are relatively expensive reactants. The photosynthetic membrane vesicle is used together with succinyl-CoA synthetase and 5-aminolevulinic acid synthase, thereby enabling the re-use of adenosine diphosphate or CoA in reaction. Accordingly, relatively expensive 5-aminolevulinic acid can be efficiently produced at low manufacturing costs from succinic acid and glycine.

12 Claims, 7 Drawing Sheets

SEQUENCE LISTING

```
<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Succinyl coenzyme A synthetase forward primer
      (SCS-F)

<400> SEQUENCE: 1
aaaaaaggtc tcgaatgaac ttacatgaat atcag                              35

<210> SEQ ID NO 2
<211> LENGTH: 38
<212> TYPE: DNA
<213> ORGANISM: Artificial Sequence
<220> FEATURE:
<223> OTHER INFORMATION: Succinyl coenzyme A synthetase reverse primer
      (SCS-R)

<400> SEQUENCE: 2
aaaaaaggtc tctgcgcttt tcagaacagt tttcagtg                           38

<210> SEQ ID NO 3
<211> LENGTH: 34
<212> TYPE: DNA
<213> ORGANISM: Artificial Sequence
<220> FEATURE:
<223> OTHER INFORMATION: 5-Aminolevulinic acid synthase forward primer
      (ALAS-F)

<400> SEQUENCE: 3
actagtggtc tcgaatggac tacaatctgg cact                               34

<210> SEQ ID NO 4
<211> LENGTH: 38
<212> TYPE: DNA
<213> ORGANISM: Artificial Sequence
<220> FEATURE:
<223> OTHER INFORMATION: 5-Aminolevulinic acid synthase reverse primer
      (ALAS-R)

<400> SEQUENCE: 4
aagcttggtc tcagcgctgg caacgacctc ggcgcgat                           38
```

CONTINUOUS PRODUCTION METHOD FOR 5-AMINOLEVULINIC ACID BY USING PHOTOSYNTHETIC MEMBRANE VESICLE

CROSS-REFERENCE TO RELATED APPLICATION

This application claims the benefit of Korean Patent Application No. 10-2014-0151907, filed on Nov. 4, 2014, in the Korean Intellectual Property Office, the disclosure of which is incorporated herein in its entirety by reference.

BACKGROUND

1. Field

The present disclosure relates to a method of continuously producing 5-aminolevulinic acid by using a photosynthetic membrane vesicle separated from photosynthetic bacteria.

2. Description of the Related Art

Depletion of modern fossil fuel has led to a necessity for development of advanced technology to use light energy as one of alternatives to fossil fuel. A source for light energy is the sun, which will not be depleted for the next few billions of years. Also, the manufacturing process for light energy does not cause pollutions, which is why light energy receives much attention as clean energy.

Photovoltaic cell apparatuses are widely used to convert light energy into electric energy. Similarly, photosynthetic bacteria have been used as devices also to convert light energy into chemical energy, which is further used for the biosynthesis of organic materials to support cell growth, and various biomaterials of high value. Once biomaterials are produced, they are either accumulated inside of photosynthetic bacteria or secreted therefrom. Studies to genetically modify the bacteria to improve the production of biomaterials are actively under way (Wang et al. 2012. Frontiers in Microbiology 3: 344). Such biomaterials include biofuel, such as fatty acid, alcohol, or hydrogen, and industrially useful compounds, such as isoprene or poly-β-hydroxybutyrate.

Photosynthesis can be classified into oxygenic and anoxygenic photosynthesis; oxygenic one is found in plants, algae, and cyanobacteria, whereas anoxygenic one is observed in purple nonsulfur bacteria, purple sulfur bacteria, green nonsulfur bacteria, green sulfur bacteria, and Heliobacteria. Bacterial photosynthetic machineries are localized to photosynthetic membranes, and examples are thylakoid membrane (TM) and intracytoplasmic membrane/invaginated chromatophore membrane (ICM).

Oxygenic photosynthesis occurs in a thylakoid membrane (TM) in bacteria. During photosynthesis, water is used as an electron donor to split into oxygen and electrons, which is mediated by light energy. Electrons are subject to flow down through a series of electron carriers, ultimately reducing the oxidized form of nicotinamide adenine dinucleotide phosphate ($NADP^+$) to the reduced form of nicotinamide adenine dinucleotide phosphate (NADPH). During the electron flow, a proton motive force is generated and used for synthesis of adenosine triphosphate (ATP) from adenosine diphosphate (ADP) and inorganic phosphate by ATP synthase. Nicotinamide adenine dinucleotide phosphate (NADPH) may be converted into nicotinamide adenine dinucleotide (NADH) by pyridine nucleotide transhydrogenase.

Purple nonsulfur bacteria performing anoxygenic photosynthesis have chromatophore membrane (ICM) in addition to plasma membrane, and the chromatophore membrane (ICM) is known as a place where photosynthesis apparatuses are exclusively localized. Photosynthesis of purple nonsulfur bacteria is performed by cyclic electron flow. When bacteriochlorophyll a in reaction center complex receives light energy, charge separation takes place to emit electron. The electron passes through a series of electron carriers and returns to bacteriochlorophyll a in reaction center. Through this process, a proton motive force is formed, and used for the synthesis of ATP from ADP and inorganic phosphate. In addition, a reverse electron flow takes place, in which oxidized nicotinamide adenine dinucleotide ($NAD^+$) is reduced to the reduced nicotinamide adenine dinucleotide (NADH) through respiratory complex I and complex II of the chromatophore membrane. Nicotinamide adenine dinucleotide (NADH) may be converted into nicotinamide adenine dinucleotide phosphate (NADPH) by pyridine nucleotide transhydrogenase.

Mature chromatophore membrane is present as an open vesicle in cell. The closed vesicle form is easily generated by cell disruption and easily purified by centrifugation (Tucker et al. 2010. Mol. Microbiol. 76: 833-847). The expressions of genes for the formation of chromatophore membrane and the biochemical process for the differentiation of cell membrane to form chromatophore membrane have been extensively studied. However, there have been no attempts to use the chromatophore membrane itself for industrial purpose. Accordingly, a practical use of the chromatophore membrane presented herein may provide a possibility for the novel use of the chromatophore membrane.

5-Aminolevulinic acid is a precursor that is first generated in the synthetic pathway of the tetrapyrroles such as heme or bacteriochlophyll. Administration of 5-aminolevulinic acid at high dose in cell leads to the formation of porphyrin-based materials at high level, which generally exhibit photosensitivity. Especially, oxidative stress (also called phototoxicity) is generated in light to show lethal effect on cell. Accordingly, 5-aminolevulinic acid is often used as herbicide and pesticide (Rebeiz et al. 1984. Enzyme Microbiol Technol. 6: 390). In particular, 5-aminolevulinic acid is also known as an environmentally-friendly herbicide due to its excellent biodegradability.

In Pharmaceutical industry, 5-aminolevulinic acid is used for the treatment of skin-related disease and also used as an additive in cosmetics. In addition, 5-aminolevulinic acid may be used for photodynamic therapy; cancerous cells can be killed by the exogenous addition of 5-aminolevulinic acid, followed by the light irradiation (Wachowska et al. 2011. Molecules 16: 4140-4164). Furthermore, 5-aminolevulinic acid can be used for bacteriostatic and bactericidal effects. For example, 5-aminolevulinic acid can be used to keep fish from viral or bacterial infection in the aquaculture industry (Korean Patent Application No. 10-2000-0024382).

Metabolic controls to produce more 5-aminolevulinic acid in *Rhodobacter sphaeroides* and *Escherichia coli* have been extensively studied (Kang et al. 2011. Bioengineered bugs 2: 6). *Zymomonas mobilis* was improved and used to synthesize the 5-aminolevulinic acid at higher level (Korean Patent Application No. 10-2011-0143640). However, 5-aminolevulinic acid in fact is produced by expensive organic synthetic methods, which are complicated and cost ineffective (Beale et al. 1979. Phytochemistry 18: 441).

The descriptions presented above as the background are used only for better understanding of the inventive concept, and shall not be regarded by one of ordinary skill in the art as admitting that they correspond to the known prior art.

SUMMARY

The synthesis of 5-aminolevulinic acid by using enzymes is simple in view that 5-aminolevulinic acid can be synthesized directly from succinic acid and glycine, which have simple structures. However, coenzymes used for the enzyme reactions may be expensive. Accordingly, the inventors of the present inventive concept have made efforts to develop a method of continuously producing 5-aminolevulinic acid by using photosynthetic bacteria, such as cyanobacteria or purple nonsulfur bacteria. As a result, the inventors found that the photosynthetic membrane vesicles separated from these bacteria constitute an apparatus for photosynthetic light reaction. The activities of succinyl-coenzyme A (CoA) synthase and 5-aminolevulinic acid synthase (ALA synthase) in the presence of the photosynthetic membrane vesicles result in the continuous production of 5-aminolevulinic acid without any further addition of the adenosine triphosphate (ATP).

Accordingly, an aspect of embodiments of the inventive concept is to provide a method of producing 5-aminolevulinic acid by using a photosynthetic membrane vesicle, succinyl-CoA synthetase and 5-aminolevulinic acid synthase.

Another aspect of embodiments of the inventive concept is to provide a method of producing 5-aminolevulinic acid, which includes light irradiation to a photosynthetic membrane vesicle to form ATP from adenosine diphosphate (ADP) and inorganic phosphate.

Another aspect of embodiments of the inventive concept is to provide a system including a vesicle of photosynthetic bacteria membrane, which continuously produces 5-aminolevulinic acid.

Another aspect of embodiments of the inventive concept is to provide a method of continuously producing 5-aminolevulinic acid, which includes the addition of succinic acid and glycine to the system.

Another aspect of embodiments of the inventive concept is to provide a composition for producing 5-aminolevulinic acid, which includes a photosynthetic membrane vesicle, succinyl-CoA synthetase, and 5-aminolevulinic acid synthase.

Other objectives and advantages of the inventive concept are clarified by the detailed description, the claims, and the drawings, which will be described below.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

An aspect of the inventive concept provides a method of producing 5-aminolevulinic acid by using a photosynthetic membrane vesicle, succinyl-coenzyme A (CoA) synthase, and 5-aminolevulinic acid synthase.

Another aspect of the inventive concept provides a composition for producing 5-aminolevulinic acid, which includes vesicle of photosynthetic bacteria membrane, succinyl-CoA synthetase, and 5-aminolevulinic acid synthase.

The inventors of the present have made efforts to develop a method of continuously producing 5-aminolevulinic acid by using photosynthetic bacteria, such as cyanobacteria or purple nonsulfur bacteria. As a result, the inventors found that the photosynthetic membrane vesicles separated from these bacteria constitute an apparatus for photosynthetic light reaction. The activities of succinyl-coenzyme A (CoA) synthase and 5-aminolevulinic acid synthase (ALA synthase) in the presence of the photosynthetic membrane vesicles result in the continuous production of 5-aminolevulinic acid without any further addition of the adenosine triphosphate (ATP).

The term "photosynthetic bacteria" used herein refers to bacteria that perform photosynthesis using light energy, and can be classified into oxygenic photosynthetic bacteria and anoxygenic photosynthetic bacteria according to electron donors. In case of oxygenic photosynthesis, water ($H_2O$) is used as an electron donor, and oxygen is produced. An example of the oxygenic photosynthetic bacteria is cyanobacteria. Cyanobacteria have thylakoid membrane (TM), which is a specific membrane structure performing photosynthesis.

The term "thylakoid membrane vesicle" used herein refers to a cell membrane unit of thylakoid membrane, which includes two kinds of photosystems and a number of proteins capable of transporting electrons, generating proton-motive force. Unlike a vesicle of a typical cell membrane, the thylakoid membrane vesicle produces ATP and nicotinamide adenine dinucleotide phosphate (NADPH) by using light energy.

The cyanobacteria from which the thylakoid membrane vesicle can be prepared are not limited, and may be cyanobacteria selected from *Synechocystis* sp., *Synechococcus* sp., *Nostoc* sp., *Anabaena* sp., *Gloeobacter* sp., and *Cyanobacterium* sp.

Anoxygenic photosynthesis is specified in that oxygen is not generated in the procedure of photosynthesis, and examples of bacteria are purple nonsulfur bacteria, purple sulfur bacteria, green nonsulfur bacteria, green sulfur bacteria, and Heliobacteria. In particular, in case of purple nonsulfur bacteria, the photosynthesis takes place in a chromatophore membrane (ICM) indented inside cell.

The term "chromatophore membrane vesicle" used herein refers to cell membrane unit of chromatophore membrane, which includes reaction center, light harvesting complex, and a number of proteins capable of transporting electrons, generating proton-motive force. Unlike a vesicle of a typical cell membrane, the chromatophore membrane vesicle produces ATP and NADPH by using light energy.

The purple nonsulfur bacteria from which the chromatophore membrane vesicle can be prepared are not limited, and may be purple nonsulfur bacteria selected from *Rhodobacter* sp., *Rhodospirillum* sp., *Rhodopseudomonas* sp., *Roseobacter* sp., *Bradyrhizobium* sp., and *Rubrivivax* sp.

Examples of *Rhodobacter* sp. purple nonsulfur bacteria are *Rhodobacter sphaeroides, Rhodobacter capsulatus, Rhodobacter apigmentum, Rhodobacter aestuarii, Rhodobacter blasticus, Rhodobacter changlensis, Rhodobacter azotoformans, Rhodobacter ovatus, Rhodobacter gluconicum, Rhodobacter johrii, Rhodobacter litoralis, Rhodobacter maris, Rhodobacter megalophilus, Rhodobacter vinaykumarii, Rhodobacter viridis, Rhodobacter massiliensis, Rhodobacter denitrificans*, and *Rhodobacter veldkampii*.

Examples of *Rhodospirillum* sp. purple nonsulfur bacteria are *Rhodospirillum rubrum, Rhodospirillum centenum, Rhodospirillum indiensis, Rhodospirillum oryzae, Rhodospirillum photometricum, Rhodospirillum molischianum*, and *Rhodospirillum sulfurexigens*.

Examples of *Rhodopseudomonas* sp. purple nonsulfur bacteria are *Rhodopseudomonas palustris, Rhodopseudomonas acidopilia, Rhodopseudomonas boonkerdii, Rhodopseudomonas faecalis, Rhodopseudomonas harwoodiae, Rhodopseudomonas julialichen, Rhodopseudomonas oryzae, Rhodopseudomonas pangongensis, Rhodopseudomonas pentothenatexigens, Rhodopseudomonas rhenobacensis*, and *Rhodopseudomonas thermotolerans*.

Examples of *Roseobacter* sp. purple nonsulfur bacteria are *Roseobacter denitrificans, Roseobacter litoralis*, and *Roseobacter prionitis*.

An example of *Bradyrhizobium* sp. purple nonsulfur bacteria is *Bradyrhizobium* sp., and an example of *Rubrivivax* sp. purple nonsulfur bacteria is *Rubrivivax gelatinosus*.

According to the inventive concept, vesicles can be obtained from thylakoid membrane and chromatophore membrane, and the separated membrane vesicles, which can perform light reaction, can be used to synthesize 5-aminolevulinic acid in vitro. Because ATP is regenerated by the vesicles in light, 5-aminolevulinic acid can be continuously produced.

Conditions for photosynthesis used herein are the ones that induce a light reaction of photosynthetic bacteria, and include appropriate light irradiation (with wavelength and intensity), temperature, and an air composition, and one of ordinary skill in the art may determine an optimal condition according to photosynthetic bacteria. For example, cyanobacteria may perform photosynthesis at temperature of about 20 to 37° C., under aerobic or anaerobic condition, at light intensity of about 5 to 500 micro Einstein/$m^2 \cdot s$ (µmole photons/$m^2 \cdot s$), and at wavelength of 400 to 700 nm. To obtain such a range of wavelength, fluorescent light lamp and LED light lamp may be used as a light source. For example, purple nonsulfur bacteria may perform photosynthesis at temperature of about 20 to 37° C., under anaerobic, aerobic or microaerobic condition, at light intensity of about 3-300 Watts/$m^2$, and at wavelength of 350 to 1000 nm. The microaerobic condition used herein refers to a condition where an oxygen partial fraction is within 5%. To obtain such a range of wavelength, incandescent light lamp and halogen lamp may be used as a light source.

Cyanobacterial thylakoid membrane vesicle includes light reaction apparatus to generate a proton motive force (pmf) cross the membrane by the electron flow in light. The pmf-derived kinetic energy enables ATP synthase to synthesize adenosine triphosphate (ATP) from adenosine diphosphate (ADP) and inorganic phosphate. In case of purple nonsulfur bacteria, a photochemical reaction is induced by light in reaction center complex, inducing cyclic electron flow, and thereby generating a proton motive force, which is used for ATP synthesis by ATP synthase.

For the synthesis of 5-aminolevulinic acid by using succinyl-CoA synthetase and 5-aminolevulinic acid synthase, ATP is required as an energy source. ATP is expensive than other substrates including succinic acid or glycine. Accordingly, it is not economical to produce 5-aminolevulinic acid by using a large amount of ATP. When used in reaction, ATP is converted into ADP. The photosynthetic bacteria membrane vesicle may convert ADP back into ATP through light reaction of photosynthesis. One of the features of the inventive concept lies in that when the photosynthetic membrane vesicle is used, ADP is re-generated by the procedure of photosynthesis of the photosynthetic membrane vesicle, allowing the continuous production of 5-aminolevulinic acid without additional supply of ATP.

Another aspect of the inventive concept provides a method of producing 5-aminolevulinic acid, which includes a) irradiating photosynthetic membrane vesicle to form ATP from ADP and inorganic phosphate; b) producing succinyl-CoA from succinic acid and CoA by using ATP energy generated in process a); c) producing 5-aminolevulinic acid from succinyl-CoA from process b); and d) re-using ADP and the inorganic phosphate from the process b) to form ATP in process a).

The conversion of ATP into ADP and the inorganic phosphate and the conversion of succinic acid and CoA into succinyl-CoA may be performed by succinyl-CoA synthetase.

The 5-aminolevulinic acid synthesis from succinyl-CoA and glycine with the release of carbon dioxide and CoA may be performed by 5-aminolevulinic acid synthase. Another feature of the inventive concept lies in the re-use of CoA to form succinyl-CoA, resulting in no need for additional supply of CoA.

The unit ratio of the specific activity of chromatophore membrane vesicle to the specific activity of succinyl-CoA synthetase and 5-aminolevulinic acid synthase is not limited, and may be in a range of 1:1 to 20:1, or 3:1 to 10:1, or 8:1. When the unit ratio of chromatophore membrane vesicle: enzyme is 8:1, 5-aminolevulinic acid may be produced at a rate that is close to the maximum speed calculated based on the specific activity of an enzyme. The term 'specific activity' of an enzyme used herein refers to a product production speed of an enzyme per protein milligram, and means a product production ability of an enzyme per protein milligram.

Another aspect of the inventive concept provides a system for continuously producing 5-aminolevulinic acid, which includes a) photosynthetic membrane vesicle that supplies ATP by photosynthetic light reaction; and b) succinyl-CoA synthetase and 5-aminolevulinic acid synthase (ALA synthase) which provides the succinyl-CoA and synthesizes 5-aminolevulinic acid.

The term "system for continuously producing 5-aminolevulinic acid" used herein refers to the system for continuously synthesizing 5-aminolevulinic acid by using the photosynthetic membrane vesicle even without an additional supply of ATP, and may include a reactor, a kit, a device, an equipment, or the like. When the system is used, the use of succinic acid and glycine alone as the substrates for the synthesis of 5-aminolevulinic acid is enough for the continuous production of 5-aminolevulinic acid in light.

In some embodiments, vesicle separated from the thylakoid membrane of cyanobacteria and the vesicle separated from the chromatophore membrane of purple nonsulfur bacteria may be used together.

The thylakoid membrane vesicle and the chromatophore membrane vesicle absorb light at different wavelengths. That is, light corresponding to the wavelength that is not absorbed by one vesicle can be absorbed by another vesicle. Accordingly, when two different photosynthetic membrane vesicles are used together, ATP may be synthesized with higher efficiency, further promoting the synthesis of 5-aminolevulinic acid. That is, combination of the vesicle from the thylakoid membrane of cyanobacteria and the vesicle from the chromatophore membrane of purple nonsulfur bacteria results in the simultaneous absorption of light at different wavelengths, visible light and the infrared light range, which leads to an increase in synthesis of 5-aminolevulinic acid.

In some embodiments, the photosynthetic membrane vesicle separated from the chromatophore membrane of purple nonsulfur bacteria is only used. Such composition is suitable for the synthesis of 5-aminolevulinic acid under anoxygenic condition.

In summary, total net reaction is as follows: 1 equivalent of succinic acid and 1 equivalent of glycine are used to produce 1 equivalent of 5-aminolevulinic acid with the release of 1 equivalent of carbon dioxide. In this regard, ADP, an inorganic phosphate, and CoA are initially added once and may be continuously re-used in reaction without additional loading of expensive ADP and CoA. Accordingly, 5-aminolevulinic acid may be continuously produced from succinic acid and glycine, which are relatively inexpensive.

Hereinafter, embodiments of the inventive concept will be described. However, these embodiments are presented herein for illustrative purpose only, and do not limit the scope of the inventive concept, which is obvious to one of ordinary skill in the art.

EXAMPLES

Example 1

Separating Chromatophore Membrane Vesicle

Figure 2:
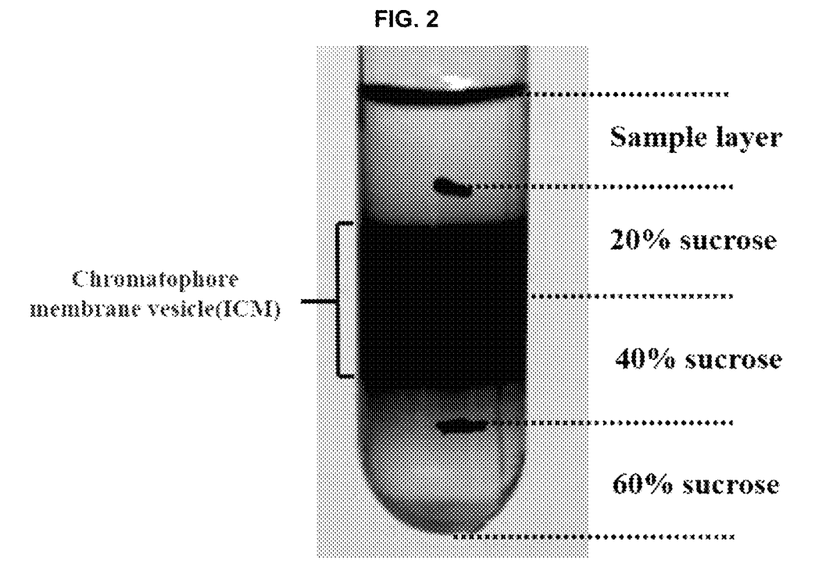
FIG. 2 shows an image of a chromatophore membrane vesicle separated by using a sucrose-density gradient ultracentrifugation according to Example 1.

In the present experiment, *Rhodobacter sphearoides* (2.4.1, ATCC BAA-808, Cohen-Bazire et al. 1956. J. Cell. Comp. Physiol. 49: 25-68), which is purple nonsulfur bacterium, was used to prepare the chromatophore membrane vesicle. For the growth of *Rhodobacter sphaeroides*, a Sistrom minimal medium (1962. J. Gen. Microbiol. 28: 607-616) was used, and a composition thereof is shown in Table 1. First, *Rhodobacter sphaeroides* strain was inoculated into a test tube containing 5 ml of Sistrom medium, and then, incubated at 30° C. with shaking at a rotation speed of 250 rpm. When the cell absorbance reached 1.0 at wavelength of 660 nm, 18 ml and screw-cap test tube was inoculated with the strain to have the absorbance of 0.05 at 660 nm. The screw-cap test tube was completely filled with medium not to allow the air to permeate thereinto, followed by closing with screw cap. The resulting test tube was incubated anaerobically at 30° C. for 18 hours in front of an incandescent light lamp at a light intensity of 15 Watts/$m^2$. Then, 8 to 9 and of the bacterial culture was inoculated into a transparent glass bottle having a capacity of 260 ml, and the bottle was completely filled with medium not to allow oxygen to permeate thereinto, followed by closing with screw cap. Then, the strain was incubated anaerobically at 30° C. for 18 hours in front of an incandescent light lamp at a light intensity of 15 Watts/$m^2$. All the subsequent steps to separate the chromatophore membrane vesicle were performed inside an anaerobic chamber (model 10, Coy laboratory product) containing gas composition of 90% nitrogen, 5% hydrogen, and 5% carbon dioxide. *Rhodobacter sphaeroides* culture in 260 ml and glass bottle was centrifuged at 4° C. and 7,000 g for 10 minutes to obtain cell pellets, which were then suspended in 4 ml and of Tris buffer (20 mM Tris, 1 mM EDTA) containing protease inhibitor cocktail (manufacturer: Roche) at the level according to the manufacturer recommendation. In subsequent procedures, the sample was placed on ice to keep it at low temperature. The cell pellets were disrupted by using a sonicator (model VCX130, Sonics & Materials) with 2 minute pulse at 100% amplification, and then, cooled on ice for 2 minutes. This process was repeatedly performed 4 times, and the resulting sample was centrifuged at 4° C. and 7,000 g for 10 minutes. The supernatant was further centrifuged by using an ultracentrifuge (Optima XE-90, Beckman Coulter) at 4° C. and 200,000 g for 1 hour. Thereafter, the resulting supernatant was discarded, and the pellet containing a chromatophore membrane vesicle was suspended in 1 ml of Tris buffer, followed by sucrose-density gradient ultracentrifugation. The sucrose-density gradient contained the most lower layer of 60% (w/v) sucrose solution in an amount of 8 me, middle layer of 40% sucrose solution in an amount of 1 ml, and the most upper layer of 20% sucrose solution in an amount of 1 ml. Then, 1 ml and sample was placed on top of the 20% sucrose layer, and was ultracentrifuged at 4° C. and 200,000 g for 4 hours. After ultracentrifugation, only a reddish brown chromatophore membrane vesicle (FIG. 2) located between the 40% and the 20% sucrose solution layer was separated therefrom, and then, diluted by using a phosphate buffer (10 mM $Na_2HPO_4$, 2 mM $KH_2PO_4$) at a ratio of 1:1. Kanamycin was added at 100 μg/ml thereto to prevent the proliferation of general contaminants, and a protease inhibitor cocktail (Roche) was added thereto at level the manufacturer recommended. The resulting chromatophore membrane vesicle was used for reaction.

TABLE 1

The composition of Sistrome minimal medium for culture of Rhodobacter sphaeroides

| Additives | Final concentration |
|---|---|
| $KH_2PO_4$ | 20 mM |
| NaCl | 8.5 mM |
| $(NH_4)_2SO_4$ | 3.78 mM |
| L-Glutamic acid | 0.67 mM |
| L-Aspartic acid | 0.25 mM |
| Succinic acid | 34 mM |
| Nitrilotriacetic acid | 1.05 mM |
| $MgCl_2 \cdot 6H_2O$ | 1.2 mM |
| $CaCl_2 \cdot 2H_2O$ | 0.23 mM |
| $FeSO_4 \cdot 7H_2O$ | 7 μM |
| $(NH_4)_6Mo_7O_{24}$ | 0.16 μM |
| EDTA | 4.7 μM |
| $ZnSO_4 7H_2O$ | 38 μM |
| $MnSO_4 H_2O$ | 9.1 μM |
| $CuSO_4 5H_2O$ | 1.6 μM |
| $Co(NO_3)_2 6H_2O$ | 0.85 μM |
| $H_3BO_3$ | 1.8 μM |
| Nicotinic acid | 8.1 μM |
| Thiamine hydrochloride | 1.5 μM |
| Biotin | 41 nM |

Example 2

Figure 3A:
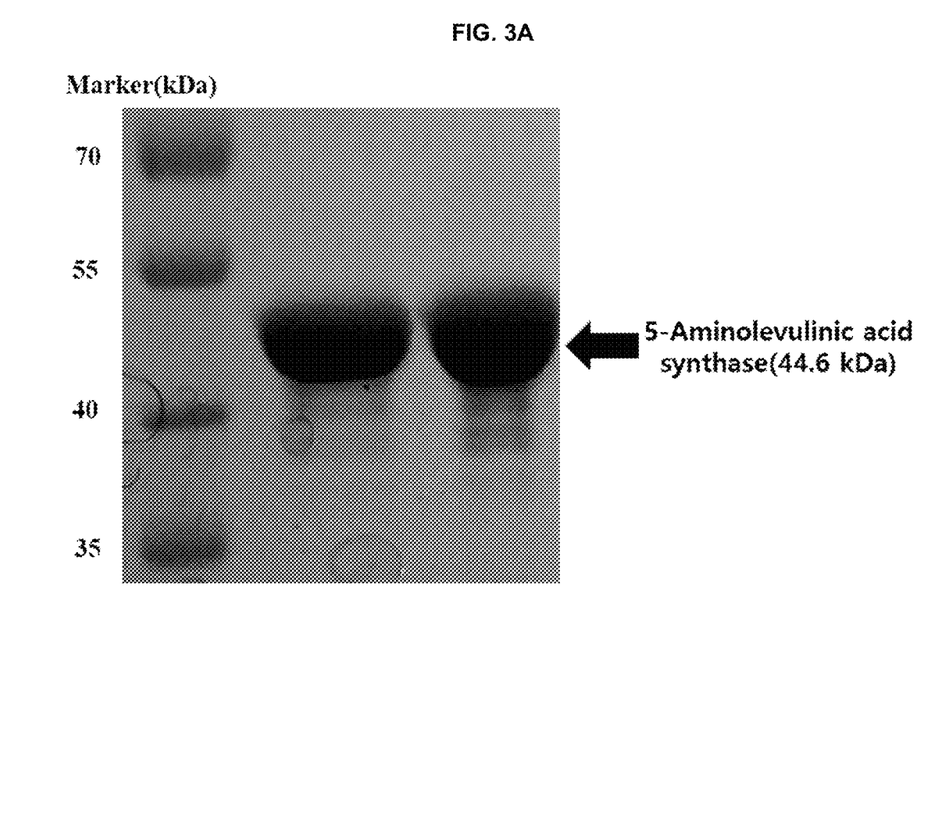
FIGS. 3A and 3B respectively show the images of 5-aminolevulinic acid synthase and succinyl-CoA synthetase, both constituting the 5-aminolevulinic acid synthetic pathway, wherein 5-aminolevulinic acid synthase and succinyl-CoA synthetase were purified and identified by polyacrylamide gel electrophoresis (SDS PAGE), and the lanes 2 and 3 in FIGS. 3A and 3B correspond to two different chromatographic fractions of the enzyme-containing supernatant.
Figure 3B:
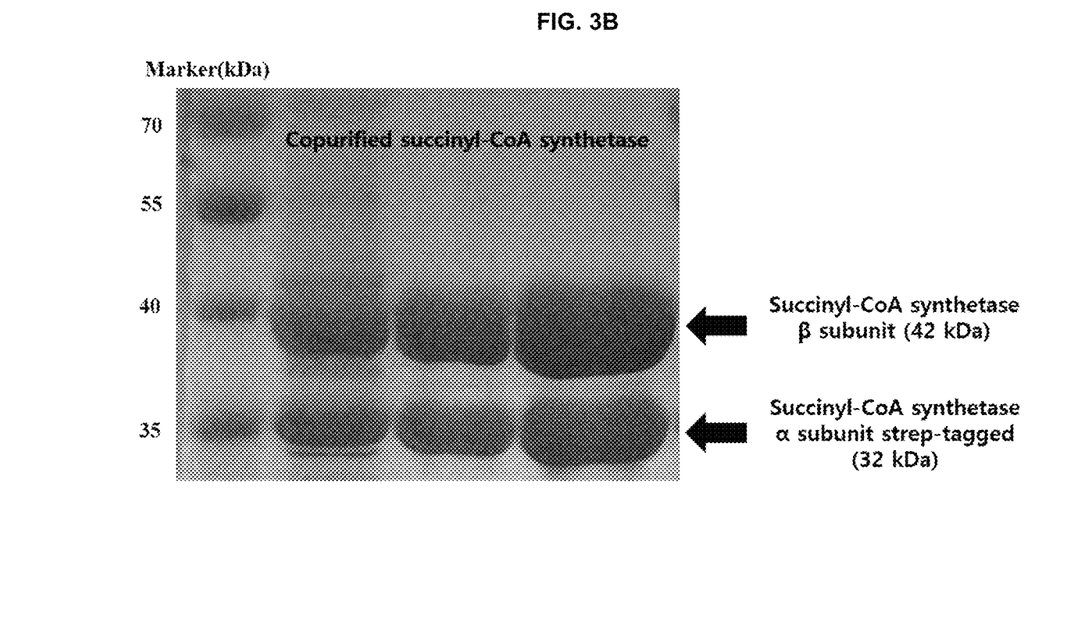

Obtaining Genes Coding Enzymes Constituting 5-Aminolevulinic Acid Synthetic Pathway In order to purify succinyl-CoA synthetase and 5-aminolevulinic acid synthase (ALA synthase) constituting a 5-aminolevulinic acid synthetic pathway, genes coding for these two enzymes were cloned in *Escherichia coli*. The gene coding for succinyl-CoA synthetase was amplified by polymerase chain reaction with chromosomal DNA of *Escherichia coli* (str. K-12 substr. MG1655) as a template, and a forward primer set forth in SEQ ID NO: 1 and a reverse primer set forth in SEQ ID NO: 2 (Table 2). At the same time, to clone the gene into an expression vector pASK-IBA3plus(IBA), recognition sequence for restriction enzyme Bsa I and an additional sequence guided by a manufacturer (IBA) were inserted at both termini of the gene. Also, to put a Strep-tag to the C-terminus of the gene, the original stop codon of the gene was removed. The gene obtained by the polymerase chain reaction was cloned into pASK-IBA3plus vector. Succinyl-CoA synthetase of *Escherichia coli* is a tetramer consisting of two α-subunits and two β-subunits, and α-subunit and β-subunit are encoded by sucD gene and sucC gene, respectively (Fraser et al. 1999. J. Mol. Biol. 285: 1633-1653). These two genes are aligned in a sequence of sucC and sucD, and a stop codon of sucC is overlapped with the start codon of sucD (pentanucleotide translational coupling, TAATG). A gene fragment obtained using SEQ ID NOS: 1 and 2 included sucC and sucD genes. When these genes are expressed, the Strep-tagged α-subunit (sucD) and β-subunit (sucC), which does not bear Strep-tag, form a tetrameric complex. Accordingly, two subunits can be co-purified (FIG. 3B).

TABLE 2

Primer for obtaining succinyl-CoA synthetase gene

| SEQ ID NO | Direction | Sequence |
|---|---|---|
| 1 | SCS-F | 5'-AAAAAAGGTCTCGAATGAACTTACATGAATAT CAG-3' |
| 2 | SCS-R | 5'-AAAAAAGGTCTCTGCGCTTTTCAGAACAGTTTTCA GTG-3' |

In case of 5-aminolevulinic acid synthase, the chromosomal DNA of purple nonsulfur bacterium *Rhodobacter sphaeroides*, was used as a template for polymerase chain reaction with forward and backward primers respectively set forth in SEQ ID NO: 3 and SEQ ID NO: 4 (Table 3). Like the succinyl-CoA synthetase, the recognition sequence for restriction enzyme Bsa I and an additional sequence recommended by the manufacturer (IBA) were inserted thereinto, and the resulting DNA was cloned into pASK-IBA3plus expression vector, thereby expressing 5-aminolevulinic acid synthase, which was Strep-tagged at its C-terminus.

TABLE 3

Primer for obtaining 5-aminolevulinic acid synthase gene

| SEQ ID NO | Direction | Sequence |
|---|---|---|
| 3 | ALAS-F | 5'-ACTAGTGGTCTCGAATGGACTACAATCTGGCACT-3' |
| 4 | ALAS-R | 5'-AAGCTTGGTCTCAGCGCTGGCAACGACCTCGGC GCGAT-3' |

Example 3

Purification of Enzymes Constituting 5-Aminolevulinic Acid Synthetic Pathway

*Escherichia coli* BL21(DE3) was transformed with the plasmid vectors for the expression of succinyl-CoA synthetase and the 5-aminolevulinic acid synthase, which were prepared according to Example 2. For purification of the enzymes, a transformed strain was inoculated into a 5 ml and of LB (Luria-Bertani) medium in test culture tube, and then, incubated at 37° C. with shaking at 250 rpm for 12 hours. Ampicillin, which is a marker for the expression vector, was added at 50 μg/ml to keep the expression vector in cell. Then, the growing culture was inoculated into a 300 ml and LB medium containing ampicillin at 50 μg/ml in 1 L flask to have the absorbance of 0.05 at 600 nm. Then the cells were cultured at 37° C. with shaking at 250 rpm until the culture absorbance reached 0.4, followed by the addition of anhydrotetracycline at 0.2 μg/ml to induce expression of the enzymes. Cells were cultured with shaking at 250 rpm for 3 more hours at 37° C. for the expression of succinyl-CoA synthetase and at 30° C. for the expression of 5-aminolevulinic acid synthase. The cells were centrifuged at 4,000 g for 10 minutes and a supernatant was removed therefrom, thereby obtaining cell pellets. The cell pellets were suspended in a 5 and buffer W (100 mM Tris-HCl, pH 8.0, 150 mM NaCl, 1 mM EDTA), and a protease inhibitor cocktail (Roche) was added thereto at level recommended by the manufacturer. To disrupt cell pellets, a sonicator (Branson sonifier 250) was used at an output pulse of 3 to the sample for 5 minutes, followed by cooling on ice for 5 minutes. This procedure was repeated three times. After centrifugation at 4° C. and 4,000 g for 10 minutes, a supernatant containing water-soluble enzymes was taken, and then subjected to affinity chromatography using Strep-tag. The purification using Strep-tag was performed in a manner recommended by the manufacturer IBA. The purified enzymes were identified by polyacrylamide gel electrophoresis as shown in FIG. 3A and FIG. 3B. Molecular weights of these two enzymes were calculated based on primary structures: a molecular weight of α-subunit of succinyl-CoA synthetase was about 32 kDa and a molecular weight of β-subunit thereof was about 42 kDa, and a molecular weight of 5-aminolevulinic acid synthase was about 45 kDa.

Example 4

Identifying Whether Chromatophore Membrane Vesicle Generates ATP

A chromatophore membrane vesicle of *Rhodobacter sphaeroides*, which is purple nonsulfur bacterium, contains all the photosynthetic apparatuses needed for photosynthetic light reaction. Accordingly, in theory, when light is irradiated to separated chromatophore membrane vesicle, photosynthetic light reaction can be performed in vitro. Light reaction of *Rhodobacter sphaeroides* is performed by cyclic electron flow, and once the cyclic electron flow is operated, a proton motive force builds up inside the vesicle. ATP synthase uses the proton motive force to synthesize ATP from ADP and an inorganic phosphate. Accordingly, the final product of the light reaction of the chromatophore membrane vesicle is ATP. In the present experiment, to experimentally confirm whether light reaction of the chromatophore membrane is operated in response to light, chromatophore membrane vesicle was irradiated and ATP formation was examined. ATP was identified by using an ATP detection kit (Sigma-Aldrich). Chromatophore membrane vesicle of purple nonsulfur bacteria contains bacteriochlorophyll a (bch a), which is a pigment required for photosynthesis. Accordingly, the chromatophore membrane vesicle was quantified by measuring the amount of bch a. First, to extract a pigment from the chromatophore membrane vesicle, 10 μl of chromatophore membrane vesicle was mixed with 490 μl of a pigment extraction solution [acetone:methanol=7:2], and then mixed well, and the mixture was centrifuged at 6,000 g for 1 minute to obtain a supernatant. Then, the absorbance of the supernatant at 770 nm was measured. The concentration (μg bch a/ml) of bch a was calculated by using the measured absorbance and the molar extinction coefficient of 83.9 mM$^{-1}$ (Kim and Lee. 2010. J Bacteriol. 192: 198-207), and then, the obtained value was used as a bch a-equivalent concentration. A chromatophore membrane vesicle solution having a final bch a-equivalent concentration of 0.15 to 0.20 mg bch a/ml was obtained in the same manner as used in Example 1. For reaction, 0.25 to 1.0 μg bch a/ml of chromatophore membrane vesicle was used. A reaction solution used for reaction consisted of 10 mM sodium phosphate (Na$_2$HPO$_4$), 2 mM potassium phosphate (KH$_2$PO$_4$), 10 mM magnesium chloride (MgCl$_2$), and 200 μM ADP. Since bch a of chromatophore membrane vesicle generally absorbs an infrared light (700 nm to 1,000 nm), incandescence light lamp emitting infrared light was used as a light source with the irradiation light intensity at 15 Watts/m$^2$. The reaction temperature was set at 30° C.

Figure 4A:
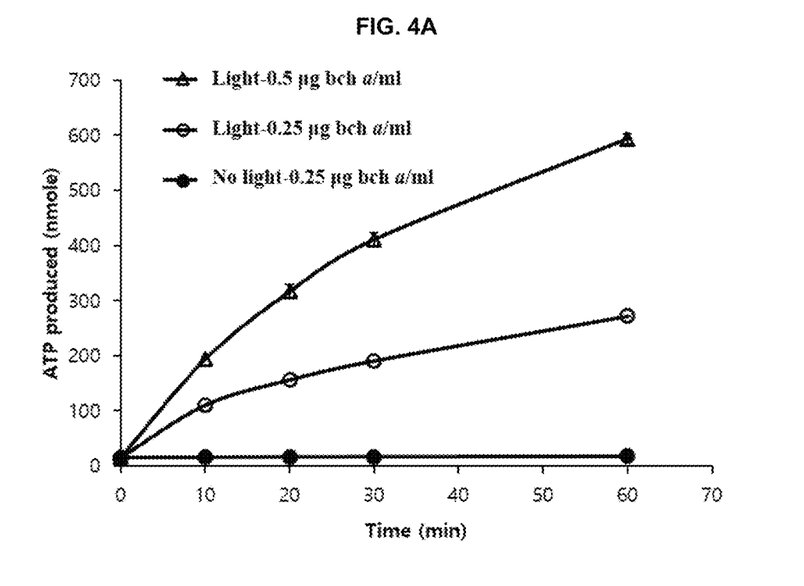
FIG. 4A is the graph illustrating the formation of adenosine triphosphate over time in the presence of varying concentrations of the chromatophore membrane vesicle in light (15 Watts/m$^2$) or in the dark.

Reaction results are shown in FIG. 4A. Only when light was irradiated (FIG. 4A, Light), ATP was generated. In the dark (FIG. 4A, No Light), ATP was not generated. These results show that the chromatophore membrane vesicle generates ATP in light-dependent way. When the amount of the chromatophore membrane vesicle was increased from 0.25 μg/ml to 0.5 μg/ml, the level of ATP formation was also increased. This result further shows that the formation of ATP was the result of the light reaction of chromatophore membrane vesicle.

Figure 4B:
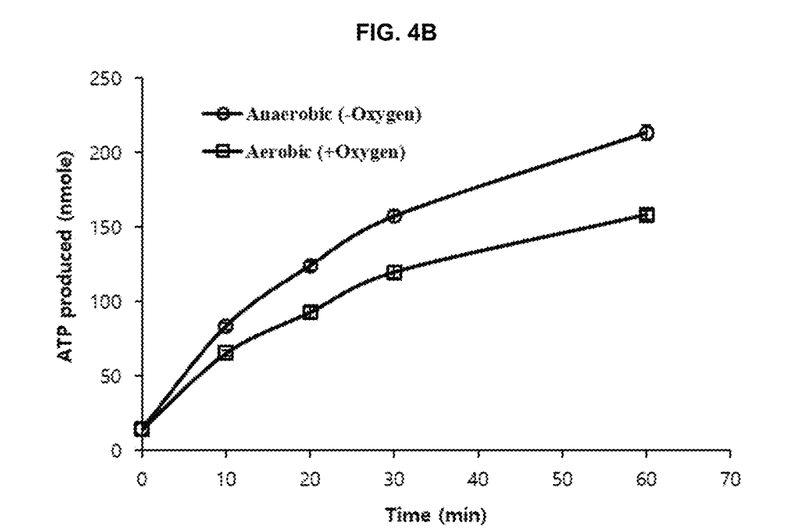
FIG. 4B is a graph of the formation of adenosine triphosphate by chromatophore membrane vesicle under anaerobic and aerobic condition.

These all reactions were performed under anaerobic conditions. This is because *Rhodobacter sphaeroides* forms a photosynthetic apparatus and performs photosynthesis only under anaerobic conditions. Accordingly, it could be assumed that under aerobic conditions, not the normal biological condition of the chromatophore membrane vesicle, the ATP formation would show a different pattern. FIG. 4B shows comparison results of ATP levels produced by using 0.25 μg bch a/ml of chromatophore membrane vesicle under aerobic and anaerobic conditions. Under aerobic condition, ATP was less produced than that observed under the anaerobic condition. This result shows that when the chromatophore membrane vesicle was used in an environment exposed to oxygen, ATP is less produced by 30%. That is, when exposed to oxygen, about 70% ATP production ability was maintained. Accordingly, it leaves at the discretion of one of ordinary skill in the art to select aerobic condition or anaerobic condition.

The chromatophore membrane vesicle separated in Example 1 had a specific activity of 4.98±0.59 nmole ATP/min/μg bch a when measured right after the vesicle preparation. One of ordinary skill in the art may adjust the amount of a chromatophore membrane by taking into consideration of a specific activity of chromatophore membrane vesicle in producing ATP.

Example 5

Confirmation of Enzymatic Activity of Succinyl-CoA Synthetase

Figure 1:
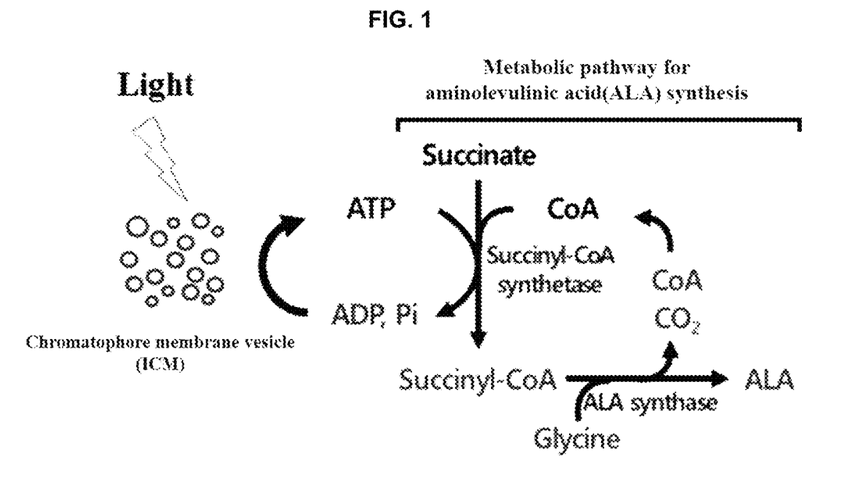
FIG. 1 is a schematic view illustrating a method of synthesizing 5-aminolevulinic acid (ALA) by using a chromatophore membrane vesicle and a 5-aminolevulinic acid synthetic pathway, wherein the 5-aminolevulinic acid synthetic pathway consists of succinyl-coenzyme A (CoA) synthase and 5-aminolevulinic acid synthase (ALA synthase)
Figure 5:
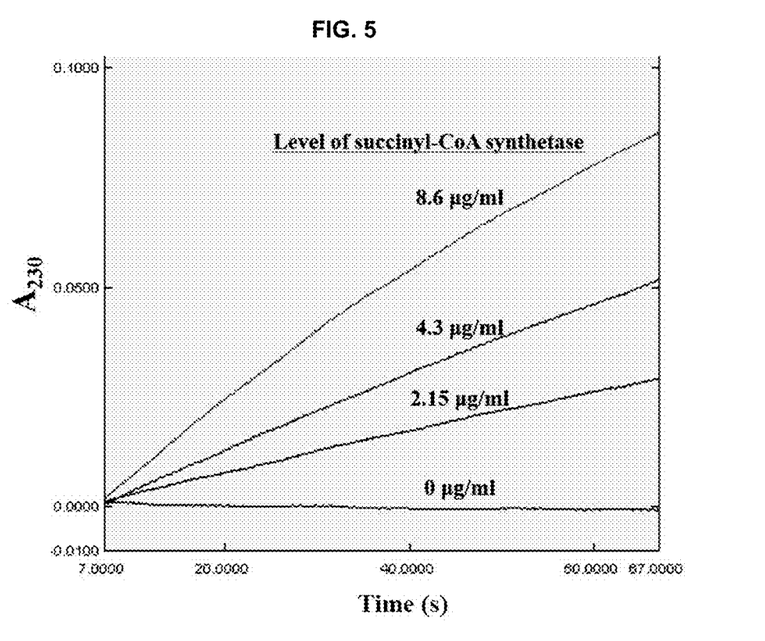
FIG. 5 shows the formation of succinyl-CoA, which is detected by the absorbance at 230 nm, against time by the varying levels of succinyl-CoA synthetase.

Succinyl-CoA synthetase, which is the first enzyme of a 5-aminolevulinic acid synthetic pathway, catalyzes the formation of succinyl-CoA and ADP form the reaction mixture of succinic acid, CoA, and ATP (FIG. 1). Succinyl-CoA synthetase may catalyze a reverse reaction. In the present experiment, it was confirmed that succinyl-CoA, which is the substrate of the second enzyme, that is, 5-aminolevulinic acid synthase, was formed by succinyl-CoA synthetase which had been purified in Example 3. The succinyl-CoA was identified by spectrophotometry. Succinyl-CoA shows a specific absorbance pattern at 230 nm. Accordingly, the formation of succinyl-CoA was confirmed by following a change in absorbance of the reaction solution at 230 nm after reaction. Also, the concentration of succinyl-CoA was determined by using a mole absorbance coefficient of 4500 M$^{-1}$ (Bridger et al. 1969. Methods Enzymol. 13: 70-75). The reaction solution consisted of 10 mM sodium phosphate, 2 mM potassium phosphate, 10 mM magnesium phosphate, 10 mM disodium succinic acid, 200 μM ATP, and 200 μM CoA, and the reaction temperature was 30° C. FIG. 5 shows a change in absorbance at 230 nm over time when different concentrations of CoA synthase was added to the reaction mixture. When the succinyl-CoA synthetase was not used (FIG. 5, 0 µg/ml), there was no change in the absorbance. However, when the enzyme was added, the absorbance was increased. As the level of succinyl-CoA synthetase was increased in reaction, the synthetic rate of succinyl-CoA was also increased (FIG. 5, 2.15, 4.3, 8.6 µg/ml). These results further show that the enzyme purified in Example 3 was the enzyme that synthesizes succinyl-CoA from succinic acid, CoA, and ATP.

Example 6

Figure 6:
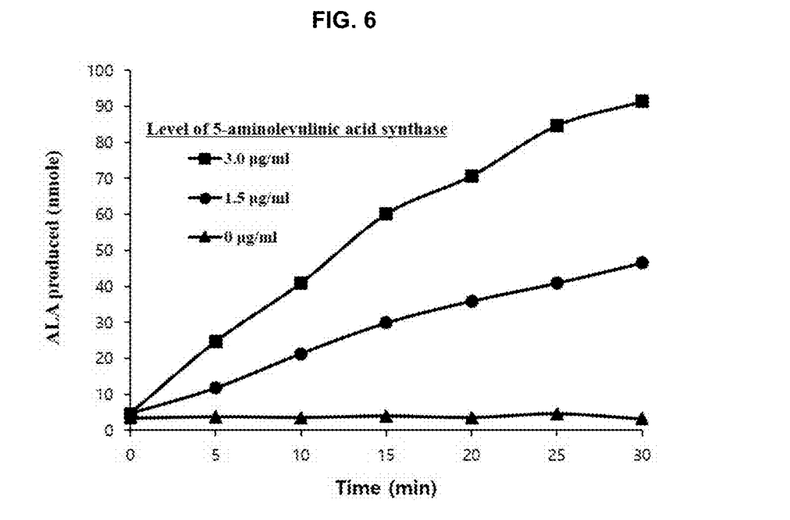
FIG. 6 shows the formation of 5-aminolevulinic acid by the varying levels of 5-aminolevulinic acid synthase.

Confirmation of Enzymatic Activity of 5-Aminolevulinic Acid Synthase 5-aminolevulinic acid synthase, which is the second enzyme of the 5-aminolevulinic acid synthetic pathway, catalyzes the condensation reaction of succinyl-CoA and glycine, each being a reaction substrate, to produce 5-aminolevulinic acid, carbon dioxide, and CoA (FIG. 1). In the present experiment, it was confirmed whether the 5-aminolevulinic acid enzyme purified in Example 3 performs the enzyme reaction to produce 5-aminolevulinic acid. The 5-aminolevulinic acid was identified by using a known method (Burnham. 1970. Methods in Enzymology 17: 195-200). The 5-aminolevulinic acid was produced at 30° C. by the varying levels of 5-aminolevulinic acid synthase in reaction mixture containing 10 mM sodium phosphate, 2 mM potassium phosphate, 10 mM magnesium phosphate, 10 mM glycine, 200 µM succinyl-CoA, and 10 µM pyridoxal phosphate. Change in the level of 5-aminolevulinic acid over time is shown in FIG. 6. When the reaction solution did not include 5-aminolevulinic acid synthase, 5-aminolevulinic acid was not produced over time. However, when the reaction solution included 5-aminolevulinic acid synthase, 5-aminolevulinic acid was produced over time, and the production rate was in proportion to the level of 5-aminolevulinic acid synthase. These results further show that the enzyme purified in Example 3 was an enzyme to synthesize 5-aminolevulinic acid from succinyl-CoA and glycine.

Example 7

Figure 7:
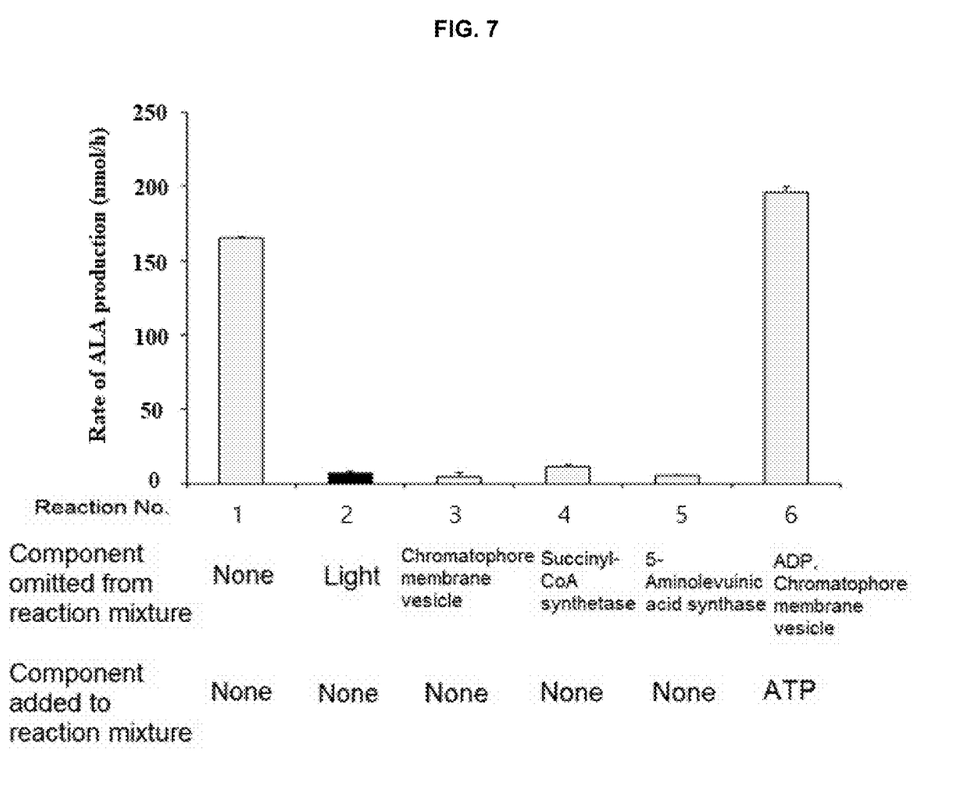
FIG. 7 shows a graph synthesizing 5-aminolevulinic acid from succinic acid and glycine by chromatophore membrane vesicle and enzymes constituting the 5-aminolevulinic acid synthetic pathway together in light at 15 Watts/m$^2$. Reaction No. 1 indicates a reaction with reaction mixture including all components, Reaction Nos. 2 to 5 indicate reactions with reaction mixtures from which a single component is omitted. Reaction No. 6 indicates a reaction without chromatophore membrane vesicle but the reaction mixture is supplemented with adenosine triphosphate instead of adenosine diphosphate.

Synthesis of 5-Aminolevulinic Acid by Using Chromatophore Membrane Vesicle and the Enzymes of the 5-Aminolevulinic Acid Synthetic Pathway Together In the present experiment, the entire reaction illustrated in FIG. 1 was performed by combining the reactions explained in Example 4, Example 5, and Example 6. A reference reaction mixture contained 10 mM sodium phosphate, 2 mM potassium phosphate, 10 mM magnesium phosphate, 10 mM glycine, 10 mM disodium succinic acid, 10 µM pyridoxal phosphate, 100 µM CoA, and 200 µM ADP. The reaction was performed at 30° C. with the light intensity of 15 Watts/m². The concentration of a chromatophore membrane vesicle used for the reaction was 3 µg bch a/ml, and the specific activities of succinyl-CoA synthetase and 5-aminolevulinic acid synthase were set at 8 nmole/min/ml each. The produced amount of 5-aminolevulinic acid was measured by using the reference reaction mixture (Reaction No. 1), and reaction mixtures (Reaction No. 2 to 6), from which a single component is omitted. The results thereof are shown in FIG. 7. In the case of the reference reaction mixture (Reaction No. 1), 5-aminolevulinic acid was produced. This result shows that the reactions illustrated in FIG. 1 was successfully performed. In case of reaction mixtures (Reaction Nos. 2 to 5), 5-aminolevulinic acid was not produced. This result shows that the reactions require light, a chromatophore membrane vesicle, succinyl-CoA synthetase, and 5-aminolevulinic acid synthase. Reaction No. 6 indicates a reaction without chromatophore membrane vesicle but the reaction mixture is supplemented with 100 µM ATP instead of ADP. The production of 5-aminolevulinic acid further shows that the chromatophore membrane vesicle functions as an ATP supplier in light.

Figure 8A:
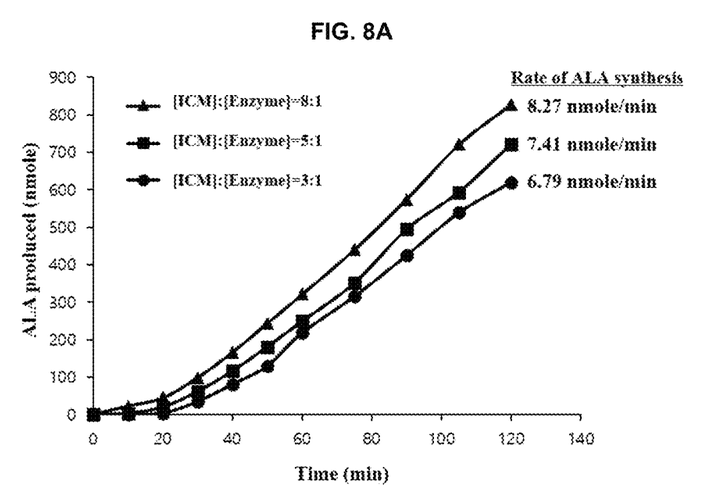
FIG. 8A shows the formation of 5-aminolevulinic acid by chromatophore membrane vesicle and enzymes constituting the 5-aminolevulinic acid synthetic pathway in light at 15 Watts/m$^2$, and in this regard, the specific activity ratios of the chromatophore membrane vesicle (ICM) to enzymes of the 5-aminolevulinic acid synthetic pathway were adjusted to be 3:1, 5:1, or 8:1 to examine the 5-aminolevulinic acid formation over time.
Figure 8B:
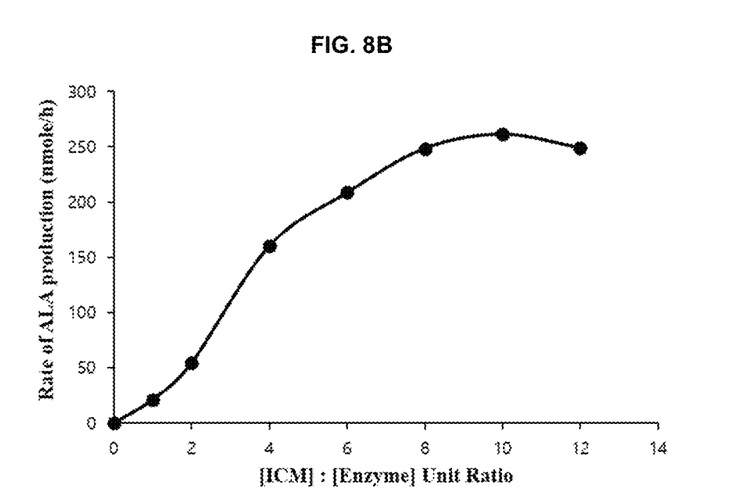
FIG. 8B shows the formation of 5-aminolevulinic acid at different specific activity ratios of chromatophore membrane vesicle to the enzymes of 5-aminolevulinic acid synthetic pathway in light at 15 Watts/m$^2$, wherein a relative ratio of the specific activity of enzymes of the 5-aminolevulinic acid synthetic pathway was fixed to 1 while that of the chromatophore membrane vesicle was varied from 0 to 12.

FIGS. 8A and 8B show the graph of the amount of 5-aminolevulinic acid with respect to a relative ratio of a chromatophore membrane vesicle (ICM) and 5-aminolevulinic acid synthetic pathway enzymes (succinyl-CoA synthetase and 5-aminolevulinic acid synthase). The relative ratio means a ratio of the specific activity of the chromatophore membrane vesicle relative to the specific activities of the synthetic pathway enzymes, which were set at 8 nmole/min each. Referring to FIG. 8B, the amount of 5-aminolevulinic acid was greatest when the specific activity of the chromatophore membrane vesicle was 8 times as high as the specific activities of the 5-aminolevulinic acid synthetic pathway enzymes. Referring to FIG. 8A, at the relative ratio of 8:1, the production rate of 5-aminolevulinic acid was 8.27 nmole/min. This value was close to 8 nmole/min, which was a maximum speed calculated based from the specific activities of the added enzymes. Accordingly, it was seen that when the relative ratio of the chromatophore membrane vesicle to 5-aminolevulinic acid synthetic pathway enzymes was 8 or more, the entire reaction was saturated with substrates.

Features and advantages of the inventive concept are summarized as follows:
  (i) the inventive concept provides a method of producing 5-aminolevulinic acid by using photosynthetic membrane vesicle, succinyl-CoA synthetase, and 5-aminolevulinic acid synthase;
  (ii) the inventive concept provides a system for continuously producing 5-aminolevulinic acid, the system including the photosynthetic membrane vesicle; and
  (iii) the function of a photosynthetic membrane vesicle is used together with the action of succinyl-CoA synthetase and 5-aminolevulinic acid synthase to re-use ADP and CoA which are expensive reactants in reaction mixture, and accordingly, relatively expensive 5-aminolevulinic acid can be produced efficiently from succinic acid and glycine which are relatively inexpensive.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of producing 5-aminolevulinic acid, the method comprising light irradiation to a photosynthetic membrane vesicle to produce adenosine triphosphate (ATP) from adenosine diphosphate (ADP) and inorganic phosphate with the use of the photosynthetic membrane vesicle, succinic acid, glycine, a succinyl-CoA synthetase, and a 5-aminolevulinic acid synthase (ALA synthase), wherein a ratio of a specific activity of the photosynthetic membrane vesicle: the specific activity of succinyl-CoA synthetase: the specific activity of the 5-aminolevulinic acid synthase is in a range of 1:1:1 to 20:1:1; and the intensity of light irradiation is 3 to 300 Watts/m².

2. The method of claim 1, wherein the method comprises:

a) irradiating light to the photosynthetic membrane vesicle to produce the ATP from the ADP and the inorganic phosphate;

b) producing succinyl-CoA from succinic acid and coenzyme A (CoA) by using energy released when the ATP in process a) is converted into the ADP and the inorganic phosphate;

c) producing 5-aminolevulinic acid from glycine and the succinyl-CoA produced in process b); and d) re-using the ADP and the inorganic phosphate produced by the conversion in process b) to form the ATP of process a).

3. The method of claim 2, wherein the photosynthetic membrane vesicle comprises vesicles selected from chromatophore membrane vesicles separated from purple non-sulfur bacteria and thylakoid membrane vesicles separated from algae and cyanobacteria.

4. The method of claim 2, wherein the process b) is performed by using succinyl-CoA synthetase as a catalyst.

5. The method of claim 4, wherein the succinyl-CoA synthetase is an enzyme that catalyzes the formation of succinyl-CoA from succinic acid and CoA and the conversion of ATP into ADP and inorganic phosphate.

6. The method of claim 2, wherein the process c) is performed by using ALA synthase as a catalyst.

7. The method of claim 6, wherein the 5-aminolevulinic acid synthase is an enzyme that catalyzes the formation of 5-aminolevulinic acid from succinyl-CoA and glycine with the release of carbon dioxide and CoA.

8. The method of claim 1, wherein the photosynthetic membrane vesicle comprises vesicles selected from chromatophore membrane vesicles separated from purple non-sulfur bacteria and thylakoid membrane vesicles separated from algae and cyanobacteria.

9. The method of claim 1, wherein the succinyl-CoA synthetase is an enzyme that catalyzes the formation of succinyl-CoA from succinic acid and CoA and the conversion of ATP into ADP and inorganic phosphate.

10. The method of claim 9, wherein the ADP is re-used in the procedure of photosynthetic light reaction of the photosynthetic membrane vesicle, so that there is no needs to add new ADP.

11. The method of claim 1, wherein the 5-aminolevulinic acid synthase is an enzyme that catalyzes the formation of 5-aminolevulinic acid from succinyl-CoA and glycine with the release of carbon dioxide and CoA.

12. The method of claim 11, wherein the CoA is re-used when succinyl-CoA is synthesized in the presence of succinyl-CoA synthetase, so that there is no needs to add new CoA.

* * * * *